(12) United States Patent
Sun et al.

(10) Patent No.: US 11,890,096 B2
(45) Date of Patent: Feb. 6, 2024

(54) METHOD FOR MEASURING FLICKER FUSION THRESHOLD BASED ON DIGITAL SET IDENTIFICATION

(71) Applicant: Civil Aviation University of China, Tianjin (CN)

(72) Inventors: Ruishan Sun, Tianjin (CN); Jing Chen, Tianjin (CN); Luping Gao, Tianjin (CN); Jingqiang Li, Tianjin (CN); Chen Zeng, Tianjin (CN); Xingchen Yan, Tianjin (CN); Xiong Chen, Tianjin (CN); Di Wu, Tianjin (CN)

(73) Assignee: Civil Aviation University of China, Tianjin (CN)

( * ) Notice: Subject to any disclaimer, the term of this patent is extended or adjusted under 35 U.S.C. 154(b) by 958 days.

(21) Appl. No.: 16/748,821

(22) Filed: Jan. 22, 2020

(65) Prior Publication Data

US 2020/0237281 A1 Jul. 30, 2020

(30) Foreign Application Priority Data

Jan. 29, 2019 (CN) .......................... 201910087082.0

(51) Int. Cl.
*A61B 5/16* (2006.01)
*A61B 3/02* (2006.01)
(52) U.S. Cl.
CPC ................ *A61B 5/161* (2013.01); *A61B 3/02* (2013.01)

(58) Field of Classification Search
None
See application file for complete search history.

(56) References Cited

U.S. PATENT DOCUMENTS

| | | | | |
|---|---|---|---|---|
| 8,713,333 | B1* | 4/2014 | Selvaraj | G11B 19/048 |
| | | | | 713/300 |
| 10,155,121 | B2* | 12/2018 | Zao | A61B 5/378 |
| 2010/0271592 | A1* | 10/2010 | Katz | A61B 5/161 |
| | | | | 351/201 |
| 2016/0192858 | A1* | 7/2016 | Min | A61B 5/316 |
| | | | | 600/545 |
| 2016/0227201 | A1* | 8/2016 | Ng | G02F 1/29 |
| 2019/0150727 | A1* | 5/2019 | Blaha | G06F 3/012 |
| 2019/0307356 | A1* | 10/2019 | Sarma | A61B 5/6803 |

* cited by examiner

*Primary Examiner* — Andre L Matthews
(74) *Attorney, Agent, or Firm* — JCIP GLOBAL INC.

(57) ABSTRACT

A method for measuring flicker fusion threshold. Set a measurement scheme, including setting N 8-shaped digital frames in a background light area that flickers within a set frequency. Set ten groups of different frequency combinations being applied to the N 8-shaped digital frames. Assign each frequency in each group of the frequency combinations with a stroke of the 8-shaped digital frame. Randomly select, for each of the N 8-shaped digital frames, one from the ten groups of the frequency combinations. Determine the value of each frequency in each group of frequency combinations in the N groups of frequency combinations. Recognize, by the subject, the flickering digits on the N 8-shaped digital frames in the background light area within the set frequency range. Determine the range of the flicker fusion threshold or the final flicker fusion threshold of the subject according to the result that can be seen by the subject.

6 Claims, 2 Drawing Sheets

METHOD FOR MEASURING FLICKER FUSION THRESHOLD BASED ON DIGITAL SET IDENTIFICATION

CROSS-REFERENCE TO RELATED APPLICATION

This application claims the priority benefit of China application serial no. 201910087082.0, filed on Jan. 29, 2019. The entirety of the above-mentioned patent application is hereby incorporated by reference herein and made a part of this specification.

Technical Field

The present invention relates to a method for measuring a flicker fusion threshold. In particular, it relates to a method for measuring a flicker fusion threshold based on digital set identification.

Background Art

Flicker fusion refers to a phenomenon in which a stimulus is not continuous but intermittent. As the intermittent frequency increases, the stimulus is no longer intermittent but continuous. We see a series of flickers, and when the number of flickers per minute is increased to a certain amount, the human eye no longer feels the flicker, but feels a fixed or continuous light. In vision, this phenomenon is called flicker fusion phenomenon. Taking a fluorescent lamp using alternating current as an example, although it flickers about 100 times per second, we do not feel it is intermittent.

The minimum frequency of the stimulus that can just cause the flicker fusion sensation (continuous light perception) is called the critical fusion frequency, also called the flicker fusion threshold.

The traditional instrument for measuring the flicker fusion threshold is generally called a bright spot scintillator. When measuring the flicker fusion threshold of a subject, the initial bright spot flicker frequency is 10.0 Hz. The subject observes the bright spot located at the center of an observation tube's vision, and continuously rotates a frequency adjustment button until the bright spot no longer flickers, but is a continuous luminous spot. The device linearly increases the flicker frequency of 0.1 Hz for flickering bright spot every time. When the subject feels that the dots are no longer flickering, he stops rotating the frequency adjuster, and records the flicker fusion frequency value at this moment. This value is the flicker fusion threshold.

The existing measurement devices and technologies have the following problems:

(1) Adjusting 0.1 Hz every time indicates that the measurement precision is only 0.1 Hz, with a low precision.

(2) The subject may have a subjective tendency, so that the measurement results may be subjectively affected.

(3) In the existing measurement method, when the flicker fusion threshold is measured, each frequency adjustment is 0.1 Hz, the measurement time is long, and the subject is prone to fatigue during a long measurement process, which affects the measurement effect.

(4) In the existing flicker fusion threshold measurement method, a cursor flickering at a fixed frequency is given for each measurement, and if you want to speed up the measurement, you need to increase the number of measurement cursors, which will increase the measurement load of the subject himself, and make the measurement process more complicated, thereby potentially affecting the measurement effect.

SUMMARY OF THE INVENTION

The technical problem to be solved by the present invention is to provide a flicker fusion threshold measurement method based on digital set identification, which is simple and fast in a testing process, and a subject can have his/her flicker fusion threshold measured quickly and accurately.

The technical solution adopted by the present invention is a method for measuring a flicker fusion threshold based on digital set identification, comprising the following steps:

1) Setting a measurement scheme, including setting N 8-shaped digital frames in a background light area that flickers within a set frequency, where the N takes on a value of 2 to 4, and assigning a name to each stroke of the 8-shaped digital frame, specifically in the 8-shaped digital frame:

Three horizontal strokes are sequentially called the first horizontal stroke, the second horizontal stroke, and the third horizontal stroke from top to bottom; a vertical stroke between the first horizontal stroke and the second horizontal stroke on the left is called the first vertical stroke; a vertical stroke between the second horizontal stroke and the third horizontal stroke on the left is called the second vertical stroke; a vertical stroke between the first horizontal stroke and the second horizontal stroke on the right is called the third vertical stroke; and a vertical stroke between the second horizontal stroke and the third horizontal stroke is called the fourth vertical stroke;

2) Setting ten groups of different frequency combinations that are applied to the N 8-shaped digital frames, respectively, wherein the frequency range of each group of frequency combinations is from 20 to 50 Hz;

3) Assigning each frequency in each group of the frequency combinations with a stroke of the 8-shaped digital frame;

4) Randomly selecting, for each of the N 8-shaped digital frames, one from the ten groups of the frequency combinations, and selecting a total of N groups, and in the N groups, the number B1 of different frequencies in the frequency group obtained by the first 8-shaped digital frame is one more than the number B of different frequencies in the frequency group obtained by the other 8-shaped digital frames;

5) Determining the value of each frequency in each group of frequency combinations in the N groups of frequency combinations described in step 4), so that different subjects can see 0 to N random digits flickering between 0 and 9 according to their own critical fusion frequencies;

6) Recognizing, by the subject, the flickering digits on the N 8-shaped digital frames in the background light area within the set frequency range; and 7) Determining the range of the flicker fusion threshold or the final flicker fusion threshold of the subject according to the 0 to N flickering digits that can be seen by the subject.

The set frequency of the background light area flickering within the set frequency described in step 1) is a frequency of 60 Hz and above.

The setting described in step 2) is ten groups of the frequency combinations applied to the N 8-shaped digital frames, comprising the following.

The first group of the frequency combinations comprising the first frequency, the second frequency, the third frequency, the fourth frequency, and the fifth frequency in an order from low to high.

The second group of the frequency combinations comprising the sixth frequency, the seventh frequency, the eighth frequency, and the ninth frequency in an order from low to high.

The third group of the frequency combinations comprising the tenth frequency, the eleventh frequency, the twelfth frequency, and the thirteenth frequency in an order from low to high.

The fourth group of the frequency combinations comprising the fourteenth frequency, the fifteenth frequency, the sixteenth frequency, and the seventeenth frequency in an order from low to high.

The fifth group of the frequency combinations comprising the eighteenth frequency, the nineteenth frequency, and the twentieth frequency in an order from low to high.

The sixth group of the frequency combinations comprising the twenty-first frequency, the twenty-second frequency, and the twenty-third frequency in an order from low to high.

The seventh group of the frequency combinations comprising the twenty-fourth frequency, the twenty-fifth frequency, and the twenty-sixth frequency in an order from low to high.

The eighth group of the frequency combinations comprising the twenty-seventh frequency and the twenty-eighth frequency in an order from low to high.

The ninth group of the frequency combinations comprising the twenty-ninth frequency and the thirtieth frequency in an order from low to high.

The tenth group of the frequency combinations comprising the thirty-first frequency and the thirty-second frequency in an order from low to high.

Assigning each frequency in each group of the frequency combinations with a stroke of the 8-shaped digital frame as described in step 3) is specifically as follows:

(1) For the first group of the frequency combinations:

The third vertical stroke and the fourth vertical stroke are given the first frequency; the first horizontal stroke is given the second frequency; the second horizontal stroke and the third horizontal stroke are given the third frequency; the first vertical stroke is given the fourth frequency; and the second vertical stroke is given the fifth frequency.

(2) For the second group of the frequency combinations:

The third vertical stroke and the fourth vertical stroke are given the sixth frequency; the first horizontal stroke is given the seventh frequency; the first vertical stroke, the second vertical stroke and the third horizontal stroke are given the eighth frequency; and the second horizontal stroke is given the ninth frequency.

(3) For the third group of the frequency combinations:

The third vertical stroke and the fourth vertical stroke are given the tenth frequency; the first vertical stroke and the second horizontal stroke are given the eleventh frequency; the first horizontal stroke and the third horizontal stroke are given the twelfth frequency; and the second vertical stroke is given the thirteenth frequency.

(4) For the fourth group of the frequency combinations:

The first horizontal stroke, the third vertical stroke and the fourth vertical stroke are given the fourteenth frequency; the second horizontal stroke and the third horizontal stroke are given the fifteenth frequency; the first vertical stroke is given the sixteenth frequency; and the second vertical stroke is given the seventeenth frequency.

(5) For the fifth group of the frequency combinations:

The first horizontal stroke, the second horizontal stroke, the third horizontal stroke, the first vertical stroke and the fourth vertical stroke are given the eighteenth frequency; the second vertical stroke is given the nineteenth frequency; and the third vertical stroke is given the twentieth frequency.

(6) For the sixth group of the frequency combinations:

The first horizontal stroke, the second horizontal stroke, the third horizontal stroke, the first vertical stroke and the fourth vertical stroke are given the twenty-first frequency; the third vertical stroke is given the twenty-second frequency; and the second vertical stroke is given the twenty-third frequency.

(7) For the seventh group of the frequency combinations:

The third vertical stroke and the fourth vertical stroke are given the twenty-fourth frequency; the first horizontal stroke, the third horizontal stroke, the first vertical stroke and the second vertical stroke are given the twenty-fifth frequency; and the second horizontal stroke is given the twenty-sixth frequency.

(8) For the eighth group of the frequency combinations:

The first horizontal stroke, the second horizontal stroke, the third horizontal stroke, the second vertical stroke and the third vertical stroke are given the twenty-seventh frequency; and the first vertical stroke and the fourth vertical stroke are given the twenty-eighth frequency.

(9) For the ninth group of the frequency combinations:

The first horizontal stroke, the second horizontal stroke, the third horizontal stroke, the first vertical stroke and the fourth vertical stroke are given the twenty-ninth frequency; and the second vertical stroke and the third vertical stroke are given the thirtieth frequency.

(10) For the tenth group of the frequency combinations:

The first horizontal stroke, the third vertical stroke and the fourth vertical stroke are given the thirty-first frequency; and the second horizontal stroke, the third horizontal stroke, the first vertical stroke, and the second vertical stroke are given the thirty-second frequency.

In step 5), the following formula is used to determine the value of each frequency in each group of frequency combinations:

$$f_{j,i} = F_0 + \Delta f'(j-1) + \Delta f(j-1), f_{1,B+1} = F_1$$

where $f_{j,i}$ refers to the value of the i-th frequency from low to high in the frequency combination obtained by the j-th 8-shaped digital frame, the value of i ranges from 1 to B, and the value of j ranges from 1 to N; $F_0$ is the lower limit of the measurement range for each round, $F_1$ is the upper limit of the measurement range for each round, the measurement range is represented by $F_0$ to $F_1$; the initial measurement range is from 20 Hz to 50 Hz; and $\Delta f'$ is the difference between the minimum frequencies of the frequency combinations obtained by two adjacent 8-shaped digital frame, and the value of $\Delta f'$ is determined by the following formula:

$$\Delta f' = \frac{(F_1 - F_0)}{B_a - 1}$$

where $B_a$ is the sum of the numbers of all different frequencies included in the N groups of frequency combinations obtained by the N 8-shaped digital frames, and the value of $B_a$ is determined by the following formula:

$$B_a = \Sigma_i^N B_j$$

where $B_j$ is the number of different frequencies in the frequency group obtained by the j-th 8-shaped digital frame, and the value of B is determined by the following formula:

$$B_2=B_3=\ldots=B_N=B, B_1=B+1$$

where $\Delta f$ is the difference between adjacent frequencies in the frequency combination obtained in the same 8-shaped digital frame, and the value of $\Delta f$ is determined by the following formula:

$$\Delta f = N*\Delta f'$$

where f1, B+1 is the highest frequency value in the frequency combination obtained by the first 8-shaped digital frame.

Step 7) includes:

(7.1) When the number of flickering digits recognized by the subject is 0, resetting the upper limit $F_1$ of the measurement range to be the minimum frequency value of the N groups of the frequency combinations that the subject does not recognize, and the lower limit of the measurement range to be $F_0=F_1-2*\Delta f$, and returning to step 4);

(7.2) When the number of flickering digits recognized by the subject is N and all of them are the digit 8, resetting the lower limit $F_0$ of the measurement range to be the maximum frequency value of the N groups of the frequency combinations recognized by the subject, and the upper limit of the measurement range to be $F_1=F_0+2*\Delta f$, and returning to step 4);

(7.3) When the number of flickering digits recognized by the subject is greater than 0 and less than N, and not all of them are the digit 8, resetting the lower limit $F_0$ of the measurement range to be the maximum frequency value of the N groups of the frequency combinations recognized by the subject, and the upper limit of the measurement range to be $F_1=F_0+\Delta f'$, determining whether $F_1-F_0$ is less than 0.2, and if so, proceeding to step (7.4), otherwise returning to step 4);

(7.4) According to the subject's flicker fusion threshold formula $(F_0+F_1)/2$ and the measurement precision formula $(F_1-F_0)/2$, obtaining the subject's flicker fusion threshold and the measurement precision, then ending the measurement.

In the method for measuring the flicker fusion threshold based on digital set identification of the present invention, each round of measurement is to recognize a fixed number of 8-shaped digital frames, and each 8-shaped digital frame contains multiple different frequencies, strokes of the same frequency can be arranged from low to high in frequency to form a total of ten different digits from 0 to 9. The subject can recognize that the digit of a frequency less than his/her own flicker fusion threshold in each 8-shaped digital frame is flickering, so that the subject's flicker fusion threshold or flicker fusion threshold range can be obtained after at most three rounds of measurement. At the same time, considering the influence of measurement precision on the final measurement result, the average of the maximum frequency value recognized by the subject and the minimum frequency value not recognized by the subject is taken as the measurement result. On this basis, the present invention has the following advantages:

1. In the present invention, when measuring the flicker fusion threshold, by setting different frequencies for each stroke in each 8-shaped digital frame, that is, each 8-shaped digital frame contains multiple different frequencies, it needs only at most 3 rounds of measurement to reduce the measurement precision value to less than 0.1, thereby improving the measurement speed.

2. In the present invention, when measuring the flicker fusion threshold, the subjective influence of the subject can be avoided, so that the measurement result is objective.

3. In the present invention, the subject recognizes 2 to 4 digits each time, reducing the subject's measurement load and simplifying the measurement process.

4. In the present invention, when each stroke contained in each 8-shaped digital frame is assigned with different frequency values, the difference between adjacent frequencies in the same 8-shaped digital frame is relatively large, and strokes corresponding to the adjacent frequencies can be combined into digits from 0 to 9, so that the subject can more clearly see which digit is flickering, which ensures a high degree of discrimination.

5. In the present invention, when calculating the final measurement result of the flicker fusion threshold, taking into account the influence of the measurement precision on the result, the final measurement result is the average of the recognized maximum frequency value and the unrecognized minimum frequency value, and the measurement precision value is half the difference between the unrecognized minimum frequency value and the recognized maximum frequency value.

6. In the present invention, the measurement is ended only when the difference between the minimum frequency value unrecognized by the subject and the recognized maximum frequency value is less than 0.2, and this method can make the final measurement precision value less than 0.1 or even much less than 0.1 after at most three rounds of measurement by setting multiple different frequencies in the 8-shaped digital frame. Therefore, the accuracy of the measurement of the flicker fusion threshold can be greatly improved.

DETAILED DESCRIPTION OF EMBODIMENTS

The method for measuring a flicker fusion threshold based on digital set identification of the present invention will be described in detail below with reference to the embodiments and the accompanying drawings.

Figure 1:
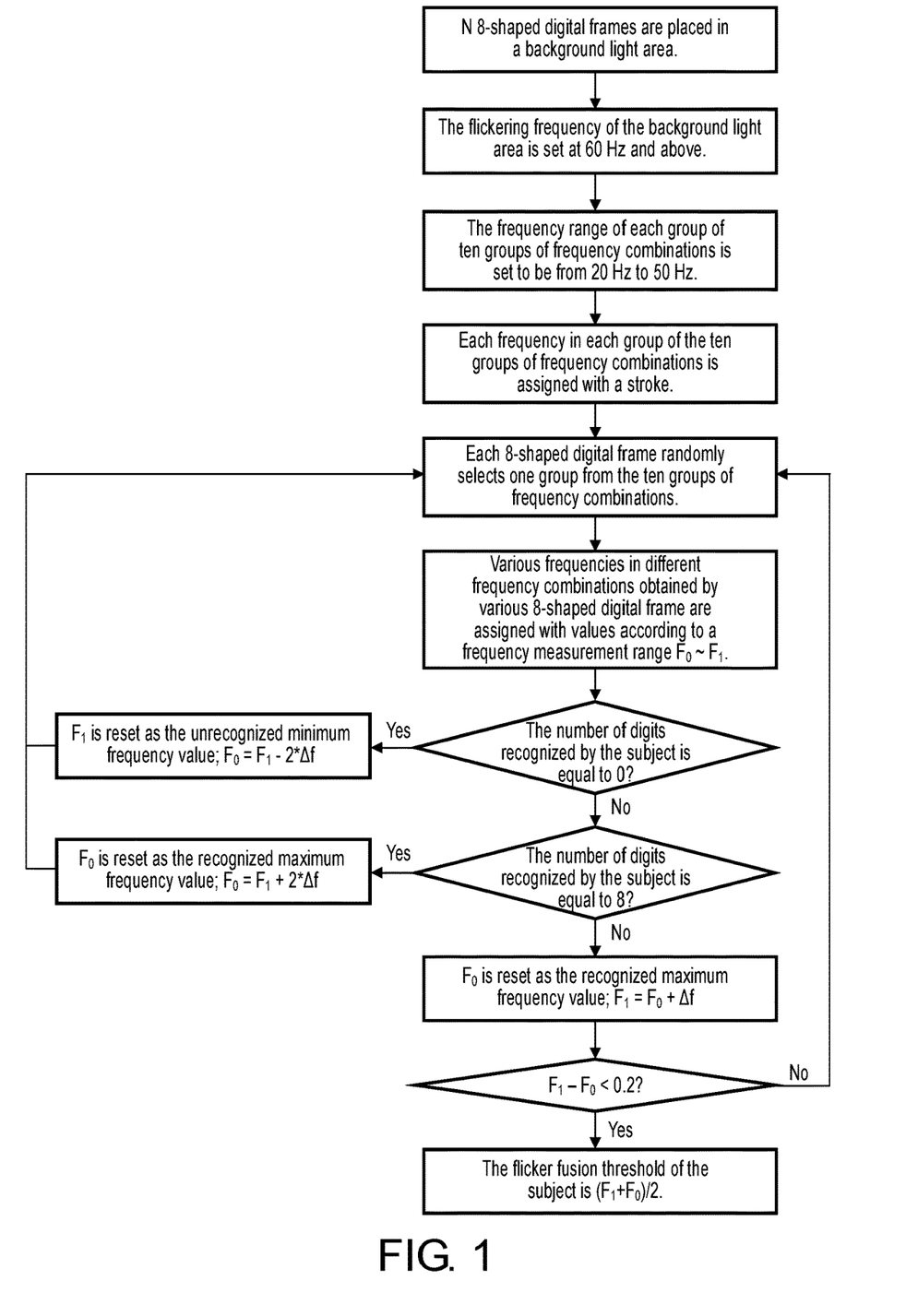
FIG. 1 is a flowchart of a method for measuring a flicker fusion threshold based on digital set identification according to the present invention.

As shown in FIG. 1, the method for measuring a flicker fusion threshold based on digital set identification of the present invention comprises the following steps:

1) Setting a measurement scheme, including setting N 8-shaped digital frames in a background light area that flickers within a set frequency, where the N takes on a value of 2 to 4, and assigning a name to each stroke of the 8-shaped digital frame, specifically in the 8-shaped digital frame.

Three horizontal strokes are sequentially called the first horizontal stroke, the second horizontal stroke, and the third horizontal stroke from top to bottom; a vertical stroke between the first horizontal stroke and the second horizontal stroke on the left is called the first vertical stroke; a vertical stroke between the second horizontal stroke and the third horizontal stroke on the left is called the second vertical stroke; a vertical stroke between the first horizontal stroke and the second horizontal stroke on the right is called the third vertical stroke; and a vertical stroke between the second horizontal stroke and the third horizontal stroke is called the fourth vertical stroke.

The set frequency of the background light area flickering within the set frequency is a frequency of 60 Hz and above.

2) Setting ten groups of different frequency combinations that are applied to the N 8-shaped digital frames respectively, wherein since the flicker fusion threshold of most people is in the range of 20 to 50 Hz, the frequency range of each group of the frequency combinations is from 20 to 50 Hz, wherein The first group of the frequency combinations includes five different frequencies comprising the first frequency, the second frequency, the third frequency, the fourth frequency, and the fifth frequency in an order from low to high.

The second group of the frequency combinations includes four different frequencies comprising the sixth frequency, the seventh frequency, the eighth frequency, and the ninth frequency in an order from low to high.

The third group of the frequency combinations includes four different frequencies comprising the tenth frequency, the eleventh frequency, the twelfth frequency, and the thirteenth frequency in an order from low to high.

The fourth group of the frequency combinations includes four different frequencies comprising the fourteenth frequency, the fifteenth frequency, the sixteenth frequency, and the seventeenth frequency in an order from low to high.

The fifth group of the frequency combinations includes three different frequencies comprising the eighteenth frequency, the nineteenth frequency, and the twentieth frequency in an order from low to high.

The sixth group of the frequency combinations includes three different frequencies comprising the twenty-first frequency, the twenty-second frequency, and the twenty-third frequency in an order from low to high.

The seventh group of the frequency combinations includes three different frequencies comprising the twenty-fourth frequency, the twenty-fifth frequency, and the twenty-sixth frequency in an order from low to high.

The eighth group of the frequency combinations includes two different frequencies comprising the twenty-seventh frequency and the twenty-eighth frequency in an order from low to high.

The ninth group of the frequency combinations includes two different frequencies comprising the twenty-ninth frequency and the thirtieth frequency in an order from low to high.

The tenth group of the frequency combinations includes two different frequencies comprising the thirty-first frequency and the thirty-second frequency in an order from low to high.

Figure 2:
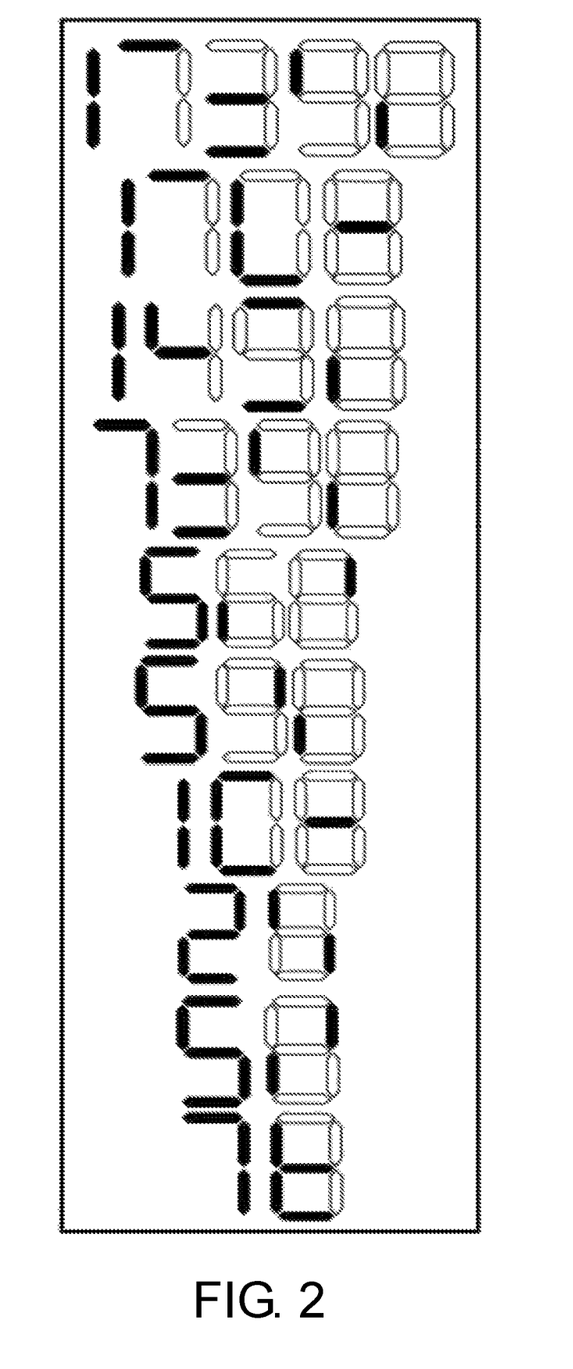
FIG. 2 is a schematic diagram of digitals composed of strokes of different frequencies in the frequency combinations of the first group to the tenth group from the top to the bottom.

3) Assigning each frequency in each group of the frequency combinations with a stroke of the 8-shaped digital frame, specifically as follows:

(1) For the first group of the frequency combinations:

The third vertical stroke and the fourth vertical stroke are given the first frequency; the first horizontal stroke is given the second frequency; the second horizontal stroke and the third horizontal stroke is given the third frequency; the first vertical stroke is given the fourth frequency; and the second vertical stroke is given the fifth frequency.

Various strokes in the 8-shaped digital frame can be combined into five digits 1, 7, 3, 9, and 8 in an order from low to high in frequency.

(2) for the second group of the frequency combinations:

The third vertical stroke and the fourth vertical stroke are given the sixth frequency; the first horizontal stroke is given the seventh frequency; the first vertical stroke, the second vertical stroke and the third horizontal stroke are given the eighth frequency; and the second horizontal stroke is given the ninth frequency.

Various strokes in the 8-shaped digital frame can be combined into four digits 1, 7, 0 and 8 in an order from low to high in frequency.

(3) For the third group of the frequency combinations:

The third vertical stroke and the fourth vertical stroke are given the tenth frequency; the first vertical stroke and the second horizontal stroke are given the eleventh frequency; the first horizontal stroke and the third horizontal stroke are given the twelfth frequency; and the second vertical stroke is given the thirteenth frequency.

Various strokes in the 8-shaped digital frame can be combined into four digits 1, 4, 9 and 8 in an order from low to high.

(4) For the fourth group of the frequency combinations:

The first horizontal stroke, the third vertical stroke and the fourth vertical stroke are given the fourteenth frequency; the second horizontal stroke and the third horizontal stroke are given the fifteenth frequency; the first vertical stroke is given the sixteenth frequency; and the second vertical stroke is given the seventeenth frequency.

Various strokes in the 8-shaped digital frame can be combined into four digits 7, 3, 9 and 8 in an order from low to high.

(5) For the fifth group of the frequency combinations:

The first horizontal stroke, the second horizontal stroke, the third horizontal stroke, the first vertical stroke and the fourth vertical stroke are given the eighteenth frequency; the second vertical stroke is given the nineteenth frequency; and the third vertical stroke is given the twentieth frequency.

Various strokes in the 8-shaped digital frame can be combined into three digits of 5, 6, and 8 in an order from low to high in frequency.

(6) For the sixth group of the frequency combinations:

The first horizontal stroke, the second horizontal stroke, the third horizontal stroke, the first vertical stroke and the fourth vertical stroke are given the twenty-first frequency; the third vertical stroke is given the twenty-second frequency; and the second vertical stroke is given the twenty-third frequency.

Various strokes in the 8-shaped digital frame can be combined into three digits of 5, 9, and 8 in an order from low to high frequency.

(7) For the seventh group of the frequency combinations:

The third vertical stroke and the fourth vertical stroke are given the twenty-fourth frequency; the first horizontal stroke, the third horizontal stroke, the first vertical stroke and the second vertical stroke are given the twenty-fifth frequency; and the second horizontal stroke is given the twenty-sixth frequency.

Various strokes in the 8-shaped digital frame can be combined into three digits of 1, 0, and 8 in an order from low to high frequency.

(8) For the eighth group of the frequency combinations:

The first horizontal stroke, the second horizontal stroke, the third horizontal stroke, the second vertical stroke and the third vertical stroke are given the twenty-seventh frequency; and the first vertical stroke and the fourth vertical stroke are given the twenty-eighth frequency.

Various strokes in the 8-shaped digital frame can be combined into two digits 2 and 8 in an order from low to high in frequency.

(9) For the ninth group of the frequency combinations:

The first horizontal stroke, the second horizontal stroke, the third horizontal stroke, the first vertical stroke and the fourth vertical stroke are given the twenty-ninth frequency; and the second vertical stroke and the third vertical stroke are given the thirtieth frequency.

Various strokes in the 8-shaped digital frame can be combined into two digits 5 and 8 in an order from low to high frequency.

(10) For the tenth group of the frequency combinations:

The first horizontal stroke, the third vertical stroke and the fourth vertical stroke are given the thirty-first frequency; the second horizontal stroke, the third horizontal stroke, the first vertical stroke and the second vertical stroke are given the thirty-second frequency.

Various strokes in the 8-shaped digital frame can be combined into two digits 7 and 8 in an order from low to high frequency.

4) Randomly selecting, for each of the N 8-shaped digital frames, one from the ten groups of the frequency combinations, and selecting a total of N groups, and in the N groups, the number B1 of different frequencies in the frequency group obtained by the first 8-shaped digital frame is one more than the number B of different frequencies in the frequency group obtained by the other 8-shaped digital frames.

5) Determining the value of each frequency in each group of frequency combinations in the N groups of frequency combinations described in step 4), so that different subjects can see 0 to N random digits flickering between 0 and 9 according to their own critical fusion frequencies;

The following formula is used to determine the value of each frequency in each group of frequency combinations:

$$f_{j,i} = F_0 + \Delta f'(j-1) + \Delta f(i-1), f_{1,B+1} = F_1$$

where $f_{j,i}$ refers to the value of the i-th frequency from low to high in the frequency combination obtained by the j-th 8-shaped digital frame, the value of i ranging from 1 to B, and the value of j ranging from 1 to N; $F_0$ is the lower limit of the measurement range for each round, $F_1$ is the upper limit of the measurement range for each round, the measurement range is expressed by $F_0$ to $F_1$, the initial measurement range is from 20 Hz to 50 Hz; and $\Delta f$ is the difference between the minimum frequencies in the frequency combinations obtained by two adjacent 8-shaped digital frames, and the value of $\Delta f'$ is determined by the following formula:

$$\Delta f' = \frac{(F_1 - F_0)}{B_a - 1}$$

where $B_a$ is the sum of the numbers of all different frequencies included in the N groups of frequency combinations obtained by the N 8-shaped digital frames, and the value of $B_a$ is determined by the following formula:

$$B_a = \Sigma_i^N B_j$$

where $B_j$ is the number of different frequencies in the frequency group obtained by the j-th 8-shaped digital frame, and the value of B is determined by the following formula:

$$B_2 = B_3 = \ldots = B_N = B, B_1 = B+1$$

where $\Delta f$ is the difference between adjacent frequencies in the frequency combination obtained in the same 8-shaped digital frame, and the value of $\Delta f$ is determined by the following formula:

$$\Delta f = N * \Delta f'$$

where f1, B+1 is the highest frequency value in the frequency combination obtained by the first 8-shaped digital frame.

6) Recognizing, by the subject, the flickering digits on the N 8-shaped digital frames in the background light area within the set frequency range; and 7) Determining the range of the flicker fusion threshold or the final flicker fusion threshold of the subject according to the 0 to N flickering digits that can be seen by the subject. comprising:

(7.1) When the number of flickering digits recognized by the subject is 0, resetting the upper limit of the measurement range to be the minimum frequency value of the N groups of different frequency combinations that the subject does not recognize, and the lower limit of the measurement range to be $F_0 = F_1 - 2*\Delta f$, and returning to step 4);

(7.2) When the number of flickering digits recognized by the subject is N, and all of them are the digit 8, resetting the lower limit $F_0$ of the measurement range to be the maximum frequency value of the N groups of different frequency combinations recognized by the subject, and the upper limit of the measurement range to be $F_1 = F_0 + 2*\Delta f$, and returning to step 4);

(7.3) When the number of flickering digits recognized by the subject is greater than 0 and less than N, and not all of them are the digit 8, resetting the lower limit $F_0$ of the measurement range to be the maximum frequency value of the N groups of different frequency combinations recognized by the subject, and the upper limit of the measurement range to be $F_1 = F_0 + \Delta f'$, determining whether $F_1 - F_0$ is less than 0.2, and if so, proceeding to step (7.4), otherwise returning to step 4);

(7.4) According to the subject's flicker fusion threshold formula $(F_0 + F_1)/2$ and the measurement precision formula $(F_1 - F_0)/2$, obtaining the subject's flicker fusion threshold and the measurement precision, then ending the measurement.

Specific examples are given below:

Example 1

(1) Three 8-shaped digital frames are placed in the background light area.

(2) According to the principle that the number of different frequencies contained in the first 8-shaped digital frame is one more than the number of different frequencies contained in the following two 8-shaped digital frames, the first 8-shaped digital frame selects the first group of frequency combinations, the second 8-shaped digital frame selects the second group of frequency combinations, and the third 8-shaped digital frame selects the third group of frequency combinations.

(3) Each frequency in each group of frequency combinations selected for the first round of measurement is assigned with a value:

The first round measurement range is from 20 Hz to 50 Hz, so that according to the formula $F_1=50$, $F_0=20$ (unit: Hz), N=3, B=4, $B_1=5$, $B_2=B_3=4$, $B_a=13$, $\Delta f'=(50-20)/(13-1)=2.5$, $\Delta f=3*2.5=7.5$, $f_{j,i}=20+\Delta f'(j-1)+\Delta f(i-1)$, (i=1, 2, 3, 4, j=1, 2, 3), various frequency values in the first group of frequency combinations of the first 8-shaped digital frame, the second group of frequency combinations of the second 8-shaped digital frame and the third group of frequency combinations of the third 8-shaped digital frame are determined as the following matrix, where $f_{j,i}$ may be expressed as a matrix of j rows and i columns, representing the value of the i-th frequency from low to high in the frequency combination selected by the j-th digital frame:

$$f_{j,i} = \begin{bmatrix} 20 & 27.5 & 35 & 42.5 \\ 22.5 & 30 & 37.5 & 45 \\ 25 & 32.5 & 40 & 47.5 \end{bmatrix}, f_{1,5} = 50$$

The four frequencies in the first row are respectively the first four different frequencies from low to high in the first group of frequency combinations selected by the first 8-shaped digital frame, that is, in the first 8-shaped digital frame, the third vertical stroke and the fourth vertical stroke are given 20 Hz; the first horizontal stroke is given 27.5 Hz; the second horizontal stroke and the third horizontal stroke are given 35 Hz; and the first vertical stroke is given 42.5 Hz; $f_{1,5}$ refers to the maximum frequency in the first group of frequency combinations selected by the first digital frame, that is, the second vertical stroke is given 50 Hz.

The four frequencies in the second row are respectively four different frequencies from low to high in the second group of frequency combinations of the second 8-shaped digital frame, that is, in the second 8-shaped digital frame, the third vertical stroke and the fourth vertical stroke are given 22.5 Hz; the first horizontal stroke is given 30 Hz; the first vertical stroke, the second vertical stroke and the third horizontal stroke are given 37.5 Hz; and the second horizontal stroke is given 45 Hz.

The four frequencies in the third row are respectively four different frequencies from low to high in the third group of frequency combinations of the third 8-shaped digital frame, that is, the third vertical stroke and the fourth vertical stroke are given 25 Hz; the first vertical stroke and the second horizontal stroke are given 32.5 Hz; the first horizontal stroke and the third horizontal stroke are given 40 Hz; and the second vertical stroke is given 47.5 Hz.

(4) The flickering digits recognized by the subject are 7, 7 and 1, respectively, that is, the first frequency 20 Hz and the second frequency 27.5 Hz in the first 8-shaped digital frame, the first frequency 22.5 Hz and the second frequency 30 Hz in the second 8-shaped digital frame, and the first frequency 25 Hz in the third 8-shaped digital frame are recognized, indicating that the maximum value of the frequency recognized by the subject in this round of measurement is 30 Hz, so that 30 Hz is selected as the lower limit of the measurement range for the next round, and the upper limit of the measurement range for the next round is: 30+2.5=32.5; that is, $F_1$=32.5; $F_0$=30, $F_1-F_0$=2.5 is not less than 0.2, so the second round of measurement is continued.

(5) In the second round of measurement, according to the principle that the number of different frequencies contained in the first 8-shaped digital frame is one more than the number of different frequencies contained in the next two 8-shaped digital frames, the first 8-shaped digital frame selects the third group of frequency combinations, the second 8-shaped digital frame selects the fifth group of frequency combinations, and the third 8-shaped digital frame selects the sixth group of frequency combinations.

(6) Each frequency in each group of frequency combinations selected for the second round of measurement is assigned with a value.

The measurement range for the second round is from 30 Hz to 32.5 Hz, so according to the formula $F_1$=32.5, $F_0$=30 (unit: Hz), N=3, B=3, $B_1$=4, $B_2=B_3$=3, $B_a$=10, Δf'=(32.5−30)/(10−1)=0.28, Δf=3*0.28=0.84, $f_{j,i}$=30+Δf(j−1)+Δf(i−1), (i=1, 2, 3, j=1, 2, 3), various frequency values in the third group of frequency combinations of the first 8-shaped digital frame, the fifth groups of frequency combinations of the second 8-shaped digital frame and the sixth groups of frequency combinations of the third 8-shaped digital frame are determined as the following matrix:

$$f_{j,i} = \begin{bmatrix} 30 & 30.84 & 31.68 \\ 30.28 & 31.12 & 31.96 \\ 30.56 & 31.4 & 32.24 \end{bmatrix}, f_{1,4} = 32.5$$

The three frequencies in the first row are respectively the first three different frequencies from low to high in the third group of frequency combinations selected by the first 8-shaped digital frame, that is, in the first 8-shaped digital frame, the third vertical stroke and the fourth vertical stroke are given 30 Hz; the first vertical stroke and the second horizontal stroke are given 30.84 Hz; and the first horizontal stroke and the third horizontal stroke are given 31.68 Hz; $f_{1,4}$ refers to the maximum frequency in the third group of frequency combinations selected by the first digital frame, that is, the second vertical stroke is given 32.5 Hz.

The three frequencies in the second row are respectively three different frequencies from low to high in the fifth group of frequency combinations of the second 8-shaped digital frame, that is, in the second 8-shaped digital frame, the first horizontal stroke, the second horizontal stroke, the third horizontal stroke, the first vertical stroke and the fourth vertical stroke are given 30.28 Hz; the second vertical stroke is given 31.12 Hz; and the third vertical stroke is given 31.96 Hz.

The three frequencies in the third row are respectively three different frequencies from the low to high in the sixth group of frequency combinations of the third 8-shaped digital frame, that is, the first horizontal stroke, the second horizontal stroke, the third horizontal stroke, the first vertical stroke and fourth vertical stroke are given 30.56 Hz; the third vertical stroke is given 31.4 Hz; and the second vertical stroke is given 32.24 Hz.

(7) The flickering digits recognized by the subject are 1, 5 and 5, respectively, that is, the tenth frequency 30 Hz in the first 8-shaped digital frame, the eighteenth frequency 30.28 Hz in the second 8-shaped digital frame, and the twenty-first frequency 30.56 Hz in the third 8-shaped digital frame are recognized, indicating that the maximum value of the frequency recognized by the subject in this round of measurement is 30.56 Hz, so that 30.56 Hz is selected as the lower limit of the measurement range for the next round, and the upper limit of the measurement range for the next round is: 30.56+0.28=30.84; that is, $F_1$=30.84; $F_0$=30.56, 30.56−30.28=0.28 is not less than 0.2, so the third round of measurement is continued.

(8) In the third round of measurement, according to the principle that the number of different frequencies contained in the first 8-shaped digital frame is one more than the number of different frequencies contained in the next two 8-shaped digital frames, the first 8-shaped digital frame selects the third group of frequency combinations, the second 8-shaped digital frame selects the sixth group of frequency combinations, and the third 8-shaped digital frame selects the fifth group of frequency combinations.

(9) Each frequency in each group of frequency combinations selected for the third round of measurement is assigned with a value:

The measurement range for the third round is from 30.56 Hz to 30.84 Hz, so according to the formula $F_1=30.84$, $F_0=30.56$ (unit: Hz), $N=3$, $B=3$, $B_1=4$, $B_2=B_3=3$, $B_a=10$, $\Delta f=(30.84-30.56)/(10-1)=0.031$, $\Delta f'=3*0.031=0.093$, $f_{j,i} = 30.56+\Delta f'(j-1)+\Delta f(i-1)$, (i=1, 2, 3, j=1, 2, 3), various frequency values in the third group of frequency combinations of the first 8-shaped digital frame, the sixth groups of frequency combinations of the second 8-shaped digital frame and the fifth groups of frequency combinations of the third 8-shaped digital frame are determined as the following matrix:

$$f_{j,i} = \begin{bmatrix} 30.56 & 30.653 & 30.746 \\ 30.591 & 30.684 & 30.777 \\ 30.622 & 30.725 & 30.808 \end{bmatrix}, f_{1,4} = 30.84$$

The three frequencies in the first row are respectively the first three different frequencies from low to high in the third group of frequency combinations selected by the first 8-shaped digital frame, that is, in the first 8-shaped digital frame, the third vertical stroke and the fourth vertical stroke are given 30.56 Hz; the first vertical stroke and the second horizontal stroke are given 30.653 Hz; and the first horizontal stroke and the third horizontal stroke are given 30.746 Hz; $f_{1,4}$ refers to the maximum frequency in the third group of frequency combinations selected by the first digital frame, that is, the second vertical stroke is given 30.84 Hz.

The three frequencies in the second row are respectively three different frequencies from the low to high in the sixth group of frequency combinations of the third 8-shaped digital frame, that is, the first horizontal stroke, the second horizontal stroke, the third horizontal stroke, the first vertical stroke and fourth vertical stroke are given 30.591 Hz; the third vertical stroke is given 30.684 Hz; and the second vertical stroke is given 30.777 Hz.

The three frequencies in the third row are respectively three different frequencies from low to high in the fifth group of frequency combinations of the second 8-shaped digital frame, that is, in the second 8-shaped digital frame, the first horizontal stroke, the second horizontal stroke, the third horizontal stroke, the first vertical stroke and the fourth vertical stroke are given 30.622 Hz; the second vertical stroke is given 30.725 Hz; and the third vertical stroke is given 30.808 Hz.

(10) The flickering digits recognized by the subject are 1 and 5, respectively, that is, the tenth frequency 30.56 Hz in the first 8-shaped digital frame, and the twenty-first frequency 30.591 Hz in the second 8-shaped digital frame are recognized, indicating that the maximum value of the frequency recognized by the subject in this round of measurement is 30.591 Hz, so that 30.591 Hz is selected as the lower limit of the measurement range for the next round, and the upper limit of the measurement range for the next round is: $30.591+0.031=30.622$; that is, $F_1=30.622$; $F_0=30.591$, $30.622-30.591=0.031$ is far less than 0.2. Finally, the flicker fusion threshold of the subject is calculated as $1/2 (30.591+30.622)=30.607$ with a measurement precision of $0.031/2=0.0155$, then the measurement ends.

What is claimed is:

1. A method for measuring flicker fusion threshold based on digital set identification, comprising the following steps:
   1) setting a measurement scheme, including setting N 8-shaped digital frames in a background light area that flickers within a set frequency, where the N takes on a value of 2 to 4, and assigning a name to each stroke of the 8-shaped digital frame, specifically in the 8-shaped digital frame:
   three horizontal strokes are sequentially called a first horizontal stroke, a second horizontal stroke, and a third horizontal stroke from top to bottom; a first vertical stroke is between the first horizontal stroke and the second horizontal stroke on the left; a second vertical stroke is between the second horizontal stroke and the third horizontal stroke on the left; a third vertical stroke is between the first horizontal stroke and the second horizontal stroke on the right; and a fourth vertical stroke is between the second horizontal stroke and the third horizontal stroke;
   2) setting ten groups of different frequency combinations that are applied to the N 8-shaped digital frames, respectively, wherein a frequency range of each group of the frequency combinations is from 20 to 50 Hz;
   3) assigning each frequency in each group of the frequency combinations with a stroke of the 8-shaped digital frame;
   4) randomly selecting, for each of the N 8-shaped digital frames, one group from the ten groups of the frequency combinations, and selecting a total of N groups, and in the N groups, a number B1 of different frequencies in the frequency group obtained by the first 8-shaped digital frame is one more than the number B of different frequencies in the frequency group obtained by the other 8-shaped digital frames;
   5) determining the value of each frequency in each group of frequency combinations in the N groups of frequency combinations described in step 4), so that 0 to N random digits flickering between 0 and 9 are presented to a subject;
   6) recognizing, by the subject, the flickering digits on the N 8-shaped digital frames in the background light area within a set frequency range; and
   7) determining the range of the flicker fusion threshold or a final flicker fusion threshold of the subject according to the 0 to N flickering digits that can be seen by the subject.

2. The method according to claim 1, wherein in step 1), the set frequency is a frequency of 60 Hz and above.

3. The method according to claim 1, wherein in step 2), the setting ten groups of the frequency combinations applied to the N 8-shaped digital frames, comprising:
   a first group of the frequency combinations comprising a first frequency, a second frequency, a third frequency, a fourth frequency, and a fifth frequency in an order from low to high;
   a second group of the frequency combinations comprising a sixth frequency, a seventh frequency, an eighth frequency, and a ninth frequency in an order from low to high;
   a third group of the frequency combinations comprising a tenth frequency, an eleventh frequency, a twelfth frequency, and a thirteenth frequency in an order from low to high;
   a fourth group of the frequency combinations comprising a fourteenth frequency, a fifteenth frequency, a sixteenth frequency, and a seventeenth frequency in an order from low to high;
   a fifth group of the frequency combinations comprising an eighteenth frequency, a nineteenth frequency, and a twentieth frequency in an order from low to high;

a sixth group of the frequency combinations comprising a twenty-first frequency, a twenty-second frequency, and a twenty-third frequency in an order from low to high;
a seventh group of the frequency combinations comprising a twenty-fourth frequency, a twenty-fifth frequency, and a twenty-sixth frequency in an order from low to high;
an eighth group of the frequency combinations comprising a twenty-seventh frequency and a twenty-eighth frequency in an order from low to high;
a ninth group of the frequency combinations comprising a twenty-ninth frequency and a thirtieth frequency in an order from low to high; and
a tenth group of the frequency combinations comprising a thirty-first frequency and a thirty-second frequency in an order from low to high.

4. The method according to claim 1, wherein in step 3), assigning each frequency in each group of the frequency combinations with the stroke of the 8-shaped digital frame as described in step 3) is specifically as follows:
(1) for the first group of the frequency combinations:
the third vertical stroke and the fourth vertical stroke are given the first frequency; the first horizontal stroke is given the second frequency; the second horizontal stroke and the third horizontal stroke are given the third frequency; the first vertical stroke is given the fourth frequency; and the second vertical stroke is given the fifth frequency;
(2) for the second group of the frequency combinations:
the third vertical stroke and the fourth vertical stroke are given the sixth frequency; the first horizontal stroke is given the seventh frequency; the first vertical stroke, the second vertical stroke and the third horizontal stroke are given the eighth frequency; and the second horizontal stroke is given the ninth frequency;
(3) for the third group of the frequency combinations:
the third vertical stroke and the fourth vertical stroke are given the tenth frequency; the first vertical stroke and the second horizontal stroke are given the eleventh frequency; the first horizontal stroke and the third horizontal stroke are given the twelfth frequency; and the second vertical stroke is given the thirteenth frequency;
(4) for the fourth group of the frequency combinations:
the first horizontal stroke, the third vertical stroke and the fourth vertical stroke are given the fourteenth frequency; the second horizontal stroke and the third horizontal stroke are given the fifteenth frequency; the first vertical stroke is given the sixteenth frequency; and the second vertical stroke is given the seventeenth frequency;
(5) for the fifth group of the frequency combinations:
the first horizontal stroke, the second horizontal stroke, the third horizontal stroke, the first vertical stroke and the fourth vertical stroke are given the eighteenth frequency; the second vertical stroke is given the nineteenth frequency; and the third vertical stroke is given the twentieth frequency;
(6) for the sixth group of the frequency combinations:
the first horizontal stroke, the second horizontal stroke, the third horizontal stroke, the first vertical stroke and the fourth vertical stroke are given the twenty-first frequency; the third vertical stroke is given the twenty-second frequency; and the second vertical stroke is given the twenty-third frequency;
(7) for the seventh group of the frequency combinations:
the third vertical stroke and the fourth vertical stroke are given the twenty-fourth frequency; the first horizontal stroke, the third horizontal stroke, the first vertical stroke and the second vertical stroke are given the twenty-fifth frequency; and the second horizontal stroke is given the twenty-sixth frequency;
(8) for the eighth group of the frequency combinations:
the first horizontal stroke, the second horizontal stroke, the third horizontal stroke, the second vertical stroke and the third vertical stroke are given the twenty-seventh frequency; and the first vertical stroke and the fourth vertical stroke are given the twenty-eighth frequency;
(9) for the ninth group of the frequency combinations:
the first horizontal stroke, the second horizontal stroke, the third horizontal stroke, the first vertical stroke and the fourth vertical stroke are given the twenty-ninth frequency; and the second vertical stroke and the third vertical stroke are given the thirtieth frequency;
(10) for the tenth group of the frequency combinations:
the first horizontal stroke, the third vertical stroke and the fourth vertical stroke are given the thirty-first frequency; and the second horizontal stroke, the third horizontal stroke, the first vertical stroke, and the second vertical stroke are given the thirty-second frequency.

5. The method according to claim 1, wherein in step 5), a value of each frequency in each group of frequency combinations is determined by the following formula:

$$f_{j,i}=F_0+\Delta f'(j-1)+\Delta f(j-1), f_{1,B+1}=F_1$$

where $f_{j,i}$ refers to a value of the i-th frequency, from low to high, in the frequency combination obtained by the j-th 8-shaped digital frame, a value of i ranges from 1 to B, and a value of j ranges from 1 to N; $F_0$ is a lower limit of a measurement range for each round, $F_1$ is an upper limit of the measurement range for each round, the measurement range is represented by $F_0$ to $F_1$; an initial measurement range is from 20 Hz to 50 Hz; and $\Delta f'$ is a difference between minimum frequencies of the frequency combinations obtained by two adjacent 8-shaped digital frame, and a value of $\Delta f'$ is determined by the following formula:

$$\Delta f' = \frac{(F_1 - F_0)}{B_a - 1}$$

where $B_a$ is a sum of numbers of all different frequencies included in the N groups of the frequency combinations obtained by the N 8-shaped digital frames, and the value of $B_a$ is determined by the following formula:

$$B_a = \sum_i^N B_j$$

where $B_j$ is a number of different frequencies in the frequency group obtained by the j-th 8-shaped digital frame, and a value of $B_j$ is determined by the following formula:

$$B_2=B_3= \ldots =B_N=B, B_1=B+1$$

where Δf is a difference between adjacent frequencies in the frequency combination obtained in the same 8-shaped digital frame, and a value of Δf is determined by the following formula:

$$\Delta f = N * \Delta f'$$

where $f_{1, B+1}$ is a highest frequency value in the frequency combination obtained by the first 8-shaped digital frame.

6. The method according to claim 1, wherein the step 7) includes:
   (7.1) when a number of flickering digits recognized by the subject is 0, resetting an upper limit $F_1$ of the measurement range to be a minimum frequency value of the N groups of the frequency combinations that the subject does not recognize, and a lower limit of the measurement range to be $F_0 = F_1 - 2*\Delta f$, and returning to step 4);
   (7.2) when the number of flickering digits recognized by the subject is N and all of them are the digit 8, resetting the lower limit $F_0$ of the measurement range to be a maximum frequency value of the N groups of the frequency combinations recognized by the subject, and the upper limit of the measurement range to be $F_1 = F_0 + 2*\Delta f$, and returning to step 4);
   (7.3) when the number of flickering digits recognized by the subject is greater than 0 and less than N, and not all of them are the digit 8, resetting the lower limit $F_0$ of the measurement range to be the maximum frequency value of the N groups of the frequency combinations recognized by the subject, and the upper limit of the measurement range to be $F_1 = F_0 + \Delta f$, determining whether $F_1 - F_0$ is less than 0.2, and if so, proceeding to step (7.4), otherwise returning to step 4);
   (7.4) according to the subject's flicker fusion threshold formula $(F_0 + F_1)/2$ and the measurement precision formula $(F_1 - F_0)/2$, obtaining the subject's flicker fusion threshold and the measurement precision, then ending the measurement.

* * * * *